United States Patent [19]

Deeg et al.

[11] Patent Number: 5,338,688
[45] Date of Patent: Aug. 16, 1994

[54] METHOD FOR THE METERED APPLICATION OF A BIOCHEMICAL ANALYTICAL LIQUID TO A TARGET

[75] Inventors: Rolf Deeg, Bernried; Eberhard Maurer, Weilheim; Reiner Babiel, Eberfing; Sigmar Klose, Berg; Bernhard Köpfer, Tutzing, all of Fed. Rep. of Germany

[73] Assignee: Boehringer Mannheim GmbH, Mannheim, Fed. Rep. of Germany

[21] Appl. No.: 19,828

[22] Filed: Feb. 19, 1993

Related U.S. Application Data

[63] Continuation of Ser. No. 735,580, Jul. 25, 1991, abandoned.

[30] Foreign Application Priority Data

Aug. 2, 1990 [DE] Fed. Rep. of Germany ....... 4024545

[51] Int. Cl.$^5$ ............................................. G01N 1/10
[52] U.S. Cl. ..................................... 436/180; 436/44; 436/46; 422/66; 422/100; 222/146.5; 222/420; 239/13
[58] Field of Search .................. 436/44, 46, 47, 54, 436/180,422; 422/63, 65, 66, 81, 100; 222/146.5, 420; 346/75, 222; 239/13, 128, 133

[56] References Cited

U.S. PATENT DOCUMENTS

| | | | |
|---|---|---|---|
| 4,376,945 | 3/1983 | Hara et al. | 346/140 R |
| 4,988,627 | 1/1991 | Smith-Lewis | 436/165 |

FOREIGN PATENT DOCUMENTS

| | | |
|---|---|---|
| 119573 | 9/1984 | European Pat. Off. . |
| 260929 | 3/1988 | European Pat. Off. . |
| 268237 | 5/1988 | European Pat. Off. . |
| 2355290 | 1/1978 | France . |
| 1218749 | 1/1971 | United Kingdom . |

Primary Examiner—James C. Housel
Assistant Examiner—Maureen M. Wallenhorst
Attorney, Agent, or Firm—Nikaido, Marmelstein, Murray & Oram

[57] ABSTRACT

A method for the metered application of a biochemical analytical liquid to a target, wherein the liquid is ejected in small quantities on to the target through a jet from a jet chamber by a procedure in which a partial volume of the liquid in the jet chamber is evaporated and expanded for a short time whenever a quantity of the liquid is to be ejected. The invention further relates to a device with a disposable jet element which contains prepackaged analytical liquid.

16 Claims, 3 Drawing Sheets

METHOD FOR THE METERED APPLICATION OF A BIOCHEMICAL ANALYTICAL LIQUID TO A TARGET

This application is a continuation of application Ser. No. 735,580 filed Jul. 25, 1991, now abandoned.

FIELD OF THE INVENTION

The invention relates to a method for the metered application of a biochemical analytical liquid to a target, wherein the liquid is ejected in small quantities on to the target through a jet, and to an appropriate device.

BACKGROUND OF THE INVENTION

In clinical chemistry, it is frequently required to carry out the metered application of an analytical liquid to a target. The liquid can be for example a sample fluid, especially blood or serum, a liquid reagent or a calibrating liquid. As a general rule, these liquids contain proteins or other macromolecules participating in biochemical processes.

The target to which the liquid is to be applied can be a reaction vessel, very small plastic reaction vessels being used predominantly in automatic analyzers at the present time. The microtitre plates often used in microbiology are a further example. One case which is of particular importance for the invention is the application of the analytical liquid to an analysis element (frequently also referred to as a test carrier or as a solid state analysis element). In terms of the present invention, this concept includes both discrete analysis elements and bands, strips or other forms of continuous analysis elements which can be passed continuously through a metering station where the analytical liquid is applied.

Traditionally, various forms of plunger-barrel constructions (dispensers and diluters) were used for the application of analytical liquids in automatic analyzers. Reagents were predominantly applied to analysis elements in such a way that a carrier matrix, for example made of paper, was immersed in a liquid reagent or, in a layering method, a reagent film was produced from a film-forming liquid containing polymers. If a spatially delimited reagent domain had to be produced specifically on a base layer, it was recommended to use various printing techniques.

EP-A-119 573 and EP-A-268 237 (U.S. Pat. No. 4,877,745) deal with methods and devices of the type indicated at the outset. Their technique is based on the ink-jet technology originally developed for computer printers (ink-jet printers). Both patent specifications contain more detailed illustrations of the previously known state of the art, to which reference is made here.

EP-A-119 573 deals especially with the problem of providing a cost-effective "pump element" designed as a disposable (single-use) component. The jet chamber here is formed essentially by a section of an elastic tube which is part of the pump element. Directed at its lateral surface is an electromagnetically actuated cylindrical rod which is moved against the tube every time a drop is to be ejected.

EP-A-268 237 describes a device in which the jet chamber consists of a length of tube which is surrounded by a coaxial piezoelectric actuating element, also of tubular design, and which is compressed when a drop is to be ejected.

SUMMARY OF THE INVENTION

An object of the invention is to provide a method or a device for the application of microquantities of biochemical analytical liquids which is less expensive than the previously known methods in terms of construction and which makes it possible very accurately to meter very small quantities (less than 1 $\mu$l) at a high frequency (more than 1000 Hz).

The object is achieved, in a method of the type indicated at the outset, by a procedure in which a partial volume of the liquid in the jet chamber is evaporated and expanded for a short time in order to eject each quantity of the liquid through the jet.

The technology on which the method according to the invention is based is known from computer printers, where it is referred to as the bubble-jet technique. In the framework of the present invention, it has been established, surprisingly, that this printing technique can be transferred to the application of analytical liquids.

The use of this technique for analytical liquids proves to be exceptionally advantageous. In particular, it is possible economically to manufacture disposable jet units which contain the analytical liquid (especially reagents or calibrating liquids) in prepacked form. This affords significant simplifications and improvements in the field of automatic analysis, as illustrated in greater detail below.

Compared with EP-A-119 573, in which the possibility of disposable "pump elements" with prepacked reagents has already been mentioned, the solution according to the present invention is distinguished especially by the fact that no mechanically moving parts whatsoever are required, resulting in increased reliability. Moreover, very small quantities of liquid can be prepared at a comparably high frequency.

Compared with EP-A-268 237, an appreciable simplification is achieved in terms of construction. The manufacturing costs are considerably lower. The cleaning of the jet channel which was necessary in the piezoelectric method is no longer applicable.

The fact that the bubble-jet technique has not yet been recommended for the metered application of biochemical analytical liquids, despite these significant advantages, could be attributable to the fact that this technique necessitates very strong heating of the analytical liquid. There is therefore a risk that the macromolecules contained in the liquid, especially protein substances, might be irreversibly damaged in their function or that denaturation or aggregate formation might occur, which would block the jets. Enzymes are particularly sensitive to strong heating. Surprisingly, however, it has been established within the framework of the present invention that the stress on the analytical liquid which is associated with the bubble-jet process does not result in any damage of practical significance to the macromolecules contained therein, or in metering problems. Thus, for example, comparative experiments in which the enzymic activity in a particular quantity of solution was determined, and this solution was then processed using the method according to the invention, produced the result that over 90% of the original activity was recovered after application to a target.

The testing of various analytical liquids has surprisingly produced the result that it is possible to work in a relatively broad viscosity range (approximately between 1 centistoke and more than 10 centistokes). This is particularly advantageous compared with the previously known ink-jet applications of analytical liquids, because a very much narrower viscosity range has to be observed in the latter case. Even as regards the surface tension, which can be influenced by the addition of detergents or suitably selected solvents, the method according to the invention has surprisingly proved to be relatively uncritical compared with the known technique.

DESCRIPTION OF THE DRAWINGS

The invention is illustrated in greater detail below with the aid of an Example which is represented schematically in the Figures.

DESCRIPTION OF THE PREFERRED EMBODIMENTS

Figure 1:
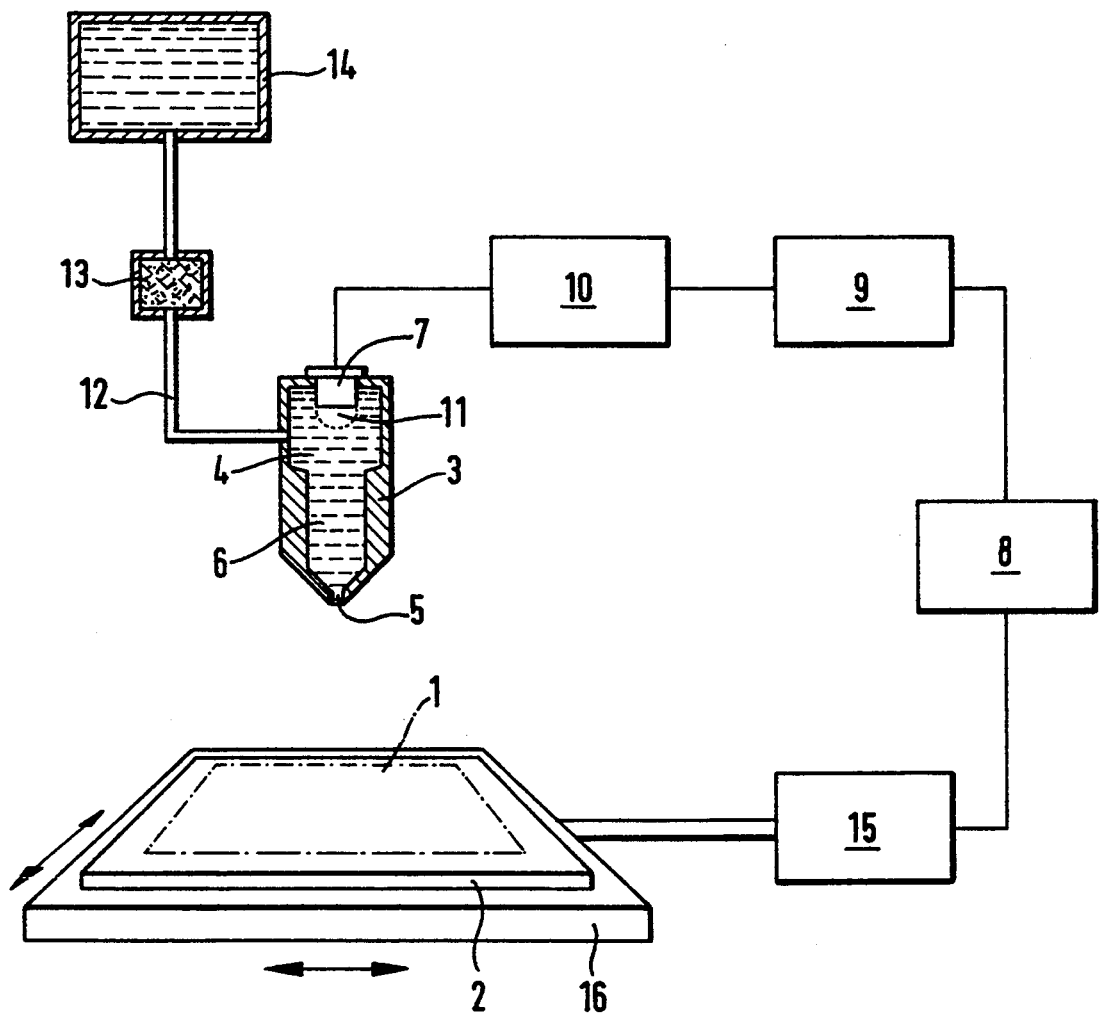
FIG. 1 is a basic diagram—partly in the form of a block diagram—of a device for the preparation of analysis elements.

FIG. 1 shows how liquid reagents can be applied to the reagent domain 1 of an analysis element 2 as a predetermined pattern of compartments. The term "compartment" denotes a delimited subdomain. Arranged over the reagent domain 1 is a jet head, denoted overall by 3, with a jet chamber 4 and a jet 5. In the jet chamber 4, there is a heating element 7 which is in thermal contact with analytical liquid 6 contained in the jet chamber 4. Controlled by a control unit 8, a current pulse is applied to the heating element 7, via a pulse generator 9 and an amplifier 10, every time a quantity of analytical liquid 6 is to be ejected from the jet 5. A vapour bubble 11 forms very rapidly (within ca. 200 $\mu$sec) and its expansion causes a drop of liquid to be ejected from the jet 5. The jet chamber 4 is connected, via a line 12 with filter 13, to a reservoir 14 for analytical liquid 6. The jet head 3, filter 13 and reservoir 14 can be accommodated in a disposable cartridge (jet unit).

With the aid of an X-Y driving mechanism 15, also controlled by the control unit 8, and a positioning table 16, the analysis element 2 can be positioned in both planar directions of the reagent domain 1 so that quantities of liquid reagent ejected successively from the jet 5 form a predetermined pattern. It will be appreciated that the jet head 3 can also be moved appropriately, either as an alternative or in addition.

In FIG. 1, a jet head 3 is shown with only one heating element 7 and one jet 5. Advantageously, however, the jet heads with several jets (usually 9, 12 or 24 jets) which are customarily employed for ink-jet printing processes can be used. This makes it possible to reduce the movement of the analysis element 2 required to produce a predetermined pattern, and to increase the metering efficiency. In particular, it is possible to produce a two-dimensional pattern of the analytical liquid 6 on the reagent domain 1 by moving the analysis element 2 relative to the jet head 3 in only one direction in space. Of course, when using a jet head 3 with several channels, the pulse generator 9 and the amplifier 10 are correspondingly of multi-channel design.

Apart from the special features described here, the structural elements known for the bubble-jet technique can be used in the invention. It is therefore unnecessary to go into the structural details of the device, especially the jet chamber, the jet or the heating elements. This information can be found in the literature on bubble-jet printers.

As explained above, a particular advantage of the invention is that it is possible to manufacture a jet unit at such a favourable cost that it can be designed as a disposable element containing a supply of analytical liquid ready for use (prepacked by the manufacturer). This eliminates expensive handling steps when performing analyses with corresponding apparatuses. Thus, with relatively little expenditure on construction, it is possible to provide analysis systems (consisting of the apparatus and specifically suited reagents) which are exceptionally versatile and easy to operate. Such a system is shown in FIG. 2 by way of example.

Figure 2:
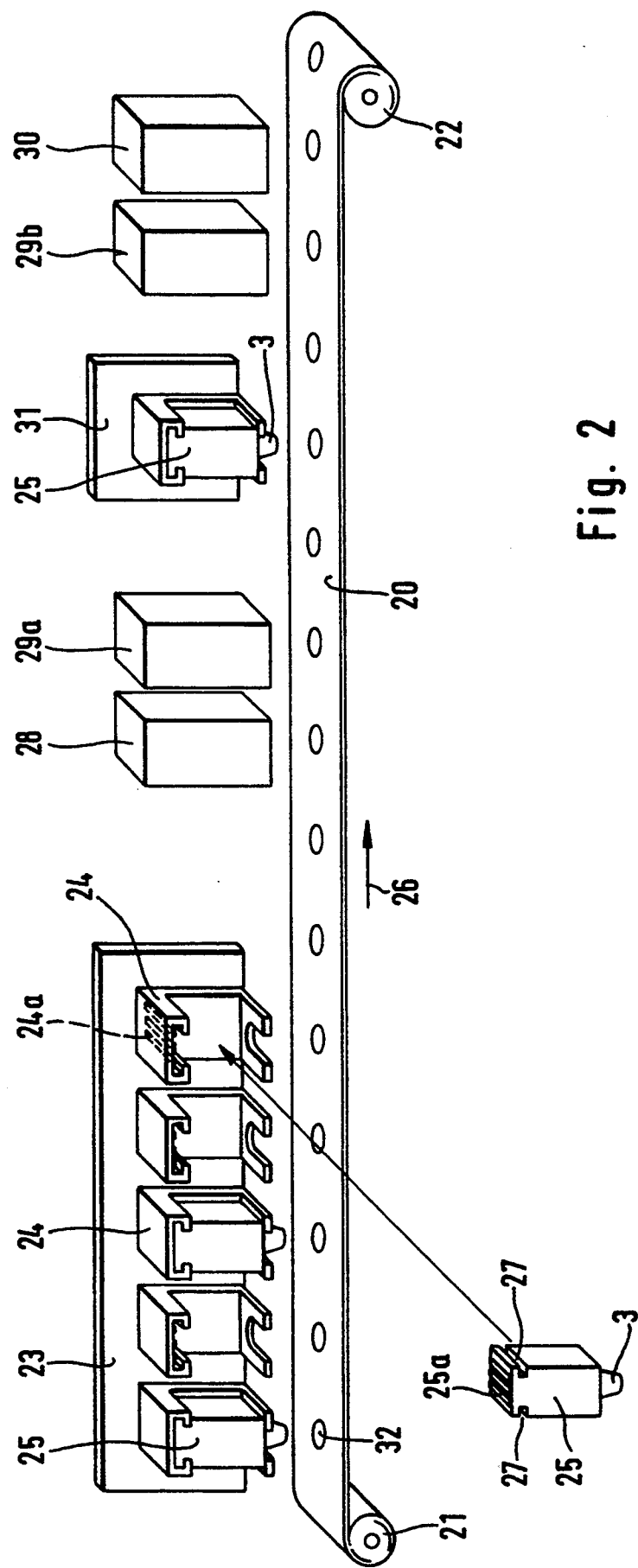
FIG. 2 is a basic diagram in perspective of an automatic analyzer based on the invention.

The analysis element used in the apparatus shown in FIG. 2 is a band 20 consisting of a suitable reagent carrier material, for example paper or a plastic film. It is conveyed step-by-step from a feed roller 21 to a pick-up roller 22. Arranged above the band 20, in a reagent metering station 23, are several holders 24 on the apparatus side, which cooperate with fixing elements 27 on the jet units 25 for bringing the latter interchangeably into defined positions above the band 20. Electrical contacts 24a, 25a are provided both on the holders 24 and on the jet units 25 so as to make an electrical connection between the apparatus and a jet unit inserted into a holder 24.

In the direction of movement of the band 20 (arrow 26), downstream from the reagent metering station 23, there are additional processing units; in the case illustrated, these are a sample metering unit 28, two wash units 29a, 29b, another reagent metering station 31 and a measuring unit 30.

The analysis procedure is started by applying analytical liquids, especially reagents, to the band 20 through one or more of the jet units 25 of the reagent metering station 23, forming reagent domains 32 on the band. To ensure the desired surface area of the reagent domains 32 perpendicularly to the direction of movement 26, the jet units 25 have several adjacent jets in their jet head 3. As an alternative or in addition, they can be moved by a mechanism (not shown) transversely to the direction of movement 26 of the band 20.

A sample is delivered through the sample metering unit 28. Where necessary, washing steps can be carried out with the wash units 29a and 29b. The reagent metering station 31 enables a further reagent to be metered. The purpose of the measuring unit 30 is to measure a physical parameter characteristic of the analysis, for example the optical reflectance or fluorescence at a particular measuring wavelength.

Further details of possible variants of the method are not discussed here. The invention can be used in a large number of different processes (e.g. homogeneous and heterogeneous immunoassays, enzymatic determinations etc.) where an analysis element, after application of the liquid reagent, is conveyed in a continuous process to a sample delivery station, a sample is brought into contact with the reaction domain and a physically measurable change occurring as a consequence of the reaction between sample and reagent is measured. This procedure has already been proposed, especially in U.S. Pat. No. 3,526,480, the disclosure of which is hereby incorporated by reference for the teachings of such procedure therein.

A decisive feature of the present invention is that, as regards the reagent delivery, a very simple and flexible adaptation to the requirements of the particular analysis is possible. Thus, by simply changing the jet units 25, the apparatus can be adapted to different analyses, working with different reagents, without having to exchange reagent containers or rinse the feed tubes and metering systems used in conventional systems. The arrangement of several jet element holders along the path of an analysis element conveyed step-by-step in a continuous process makes it possible, on the one hand, to meter several different reagents at different points in time and, on the other hand, even for an individual reagent, easily to adapt the time between application to the analysis element and sample delivery to the particular requirements.

A set-up of such simplicity has only been possible hitherto by using prepared analysis elements such as those conventionally used especially in the external form of test strips or as analysis slides. However, this necessitated an expensive conveying mechanism for the analysis elements. Furthermore, the analysis elements had to be stored for prolonged periods between manufacture and use. In view of the problematical storage stability of such analysis elements, this carries a high cost. By virtue of the invention, the analysis element with a reagent domain containing the desired reagent combination can easily be freshly prepared immediately before use (i.e. before the sample is delivered).

The continuously conveyed analysis element does not necessarily have to be in the form of a band. Depending on the requirements of the analysis, it would also be possible to use small reaction vessels, for example in the form of shallow plastic dishes linked together, or other continuously conveyable reagent carriers.

The invention can advantageously be used for the application of a very wide variety of reagents, conventionally employed in clinical chemistry, to a solid carrier. For example, enzymes, substrates or other soluble reaction components can be applied to the carrier in such a way as to be readily elutable in order to react in the liquid phase. However, the invention can also advantageously be used for the application of reagents which are bound to the carrier (especially antibodies, antigens etc.). Finally, it can be convenient if reaction components are first applied by other methods to the carrier surface to which the application by the method according to the invention is carried out. Thus, for example, a carrier material can be provided over a large area with a surface coating containing streptavidin, to which selectively and specifically biotinylated reagents are applied, the reagents being bound to the carrier via the biotin-streptavidin bond. Further details are described in U.S. patent application entitled "Analysis element and process for its manufacture" (Attorney docket no. 910920) filed of even date herewith by the present inventors, which is hereby incorporated by reference for the teachings of such materials and methods therein.

If, using the method according to the invention, several different liquid reagents are applied to a reagent domain, it is advantageous to choose the pattern of application in such a way that the compartments produced by quantities of different liquid reagents do not come into mutual contact. This applies especially if the reagents contained in the liquids interfere with one another (at least in the liquid state). In this case, the quantities of different liquid reagents preferably form a pattern of alternating compartments so that they are close together but nevertheless spatially separated. In this respect, reference is again made to the simultaneously filed patent application.

Figure 3:
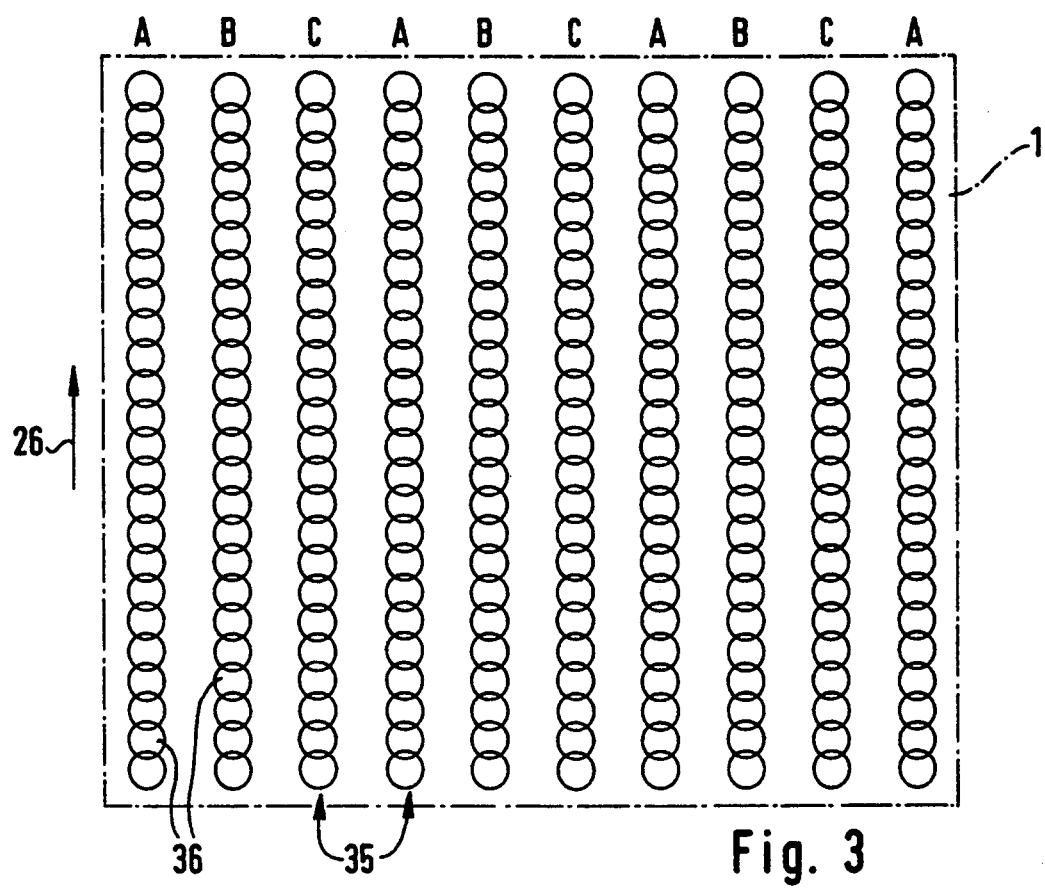
FIG. 3 is an overhead view showing a reagent domain of an analysis element.

Such a pattern of compartments is shown in FIG. 3.

In the Example illustrated, the quantities of liquid reagent form several rows of compartments 35, each consisting of many dots 36 arranged close together, and each dot being produced by a quantity of the liquid reagent. For the case where the liquid reagent is applied to the carrier in a continuous process, as shown in FIG. 2, the different compartments of the same reagent composition can conveniently be ejected from different jets in the same jet unit 25. The direction of movement is parallel to the rows (arrow 26) in this case.

The letters indicated at the top edge of FIG. 3 denote three different sets—A, B, C—of compartments 35, where the compartments 35 in the same set contain the same reagents and the reagents in different sets differ in this chemical composition.

Other forms of dots can also be used instead of the alternating rows shown. In particular, a spot pattern consisting of dots which do not mutually overlap (so that each dot forms one compartment) can be convenient.

In the Example illustrated, the dots within the compartments are little more than 0.1 mm apart. The distance between the compartments is ca. 0.26 mm. Only every other one of the compartments producible by the printing technique was used. In principle, the distance between the dots can be even smaller.

Within the framework of the present invention, it has been established that such a dense arrangement, produced by the method according to the invention, of dots consisting of different liquid reagents makes it possible in many cases to perform advantageous analytical procedures. Insofar as different mutually incompatible reagents have hitherto been used in one analysis element, they have usually been integrated into different layers of a multilayer analysis element, these layers either having been prepared separately and then combined together or having been successively applied to a base layer in a layering process. In fact, it has already been proposed in DE-C2-27 29 333 to apply mutually incompatible reagents to a surface, by the screen printing process, in such a way that the dots alternate. This known process is very expensive, however, and demands long reaction times. The method according to the invention makes it possible easily to produce such a small distance between the dots that, after delivery of the sample, the different reagents rapidly mix virtually completely and react homogeneously.

The following Examples serve to illustrate the invention further.

EXAMPLE 1

The ink from an ink-jet printing head working on the bubble-jet principle (Hewlett-Packard Quiet Jet plus) is exchanged for a tartrazine dye solution.

Data for the printing head:
— 12 jets arranged in a row
— drop diameter: ca. 75 $\mu$m
— smallest meterable quantity (1 drop): 230 picoliters
— maximum print density per printing step: 192×192 drops/inch$^2$ This printing head is accommodated together with an ink reservoir in a removable cartridge. The printing head is controlled via a personal computer with the aid of a Basic control program.

Volumes of between 0.1 and 5 µl of the dye solution (40 mg/ml of tartrazine in 40 mM sodium phosphate buffer (NaPB) pH 7.4) were metered into test tubes filled with 2 ml of distilled water. The components were then carefully mixed within a commercially available analyzer (ES 22 from Boehringer Mannheim GmbH) and the extinction at 405 nm was measured. 15 determinations were carried out in order to calculate the precision of the metering. The results are shown in Table 1.

EXAMPLE 2

In this Example, a solution of 0.5 mg/ml of the enzyme peroxidase in 40 mM NaPB pH 7.4, 3% by weight of polyvinylpyrrolidone and 0.01% by weight of Triton-X-100 was metered analogously to Example 1. In this case, each of the tubes already contained 2 ml of ABTS® substrate solution (1.9 mmol/l of 2,2′-azinodi[3-ethylbenzothiazoline-6-sulphonic acid]diammonium salt; 100 mmol/l of phosphate-citrate buffer pH 4.4; 2.2 mmol/l of sodium perborate). The metered volumes were between 0.23 and 80 nl. The extinctions and metering precisions were determined analogously to Example 1.

The results of Example 2 are shown in Table 2.

TABLE 1

| VOLUME (µl) | 0.1 | 0.2 | 0.6 | 2 | 5 |
|---|---|---|---|---|---|
| CV (%) | 1.4 | 0.96 | 0.63 | 0.57 | 0.65 |

TABLE 2

| VOLUME (nl) | 0.23 | 0.46 | 1 | 20 | 80 |
|---|---|---|---|---|---|
| CV (%) | 7.77 | 4.95 | 3.84 | 4.1 | 1.98 |

Each of the Tables indicates the nominal volume and the coefficient of variation CV. The CV values, which are based on 15 measurements in each case, show that the precision of the metering (relative to the very small volumes) is excellent.

EXAMPLE 3

A liquid reagent of the following composition:
100 mM Tris/HCl pH 7.9
15 mM tribromohydroxybenzoic acid
5 mM 3-methyl-2-benzo-(2′-sulpho)-thiazolinone hydrazone
50 U/ml sarcosine oxidase
10 U/ml peroxidase
is processed with a printing head corresponding to Examples 1 and 2. The coating solution is applied to an absorbent paper with the maximum print density (192×192 drops/inch$^2$), producing six separate reagent domains. The application is repeated three times, the total amount of liquid reagent applied being about 3.9 µl/cm2. The paper is then dried at room temperature (ca. 30 min) or the sample is applied immediately.

If 1 µl of sample with varying sarcosine concentrations of between 0 and 100 mM is applied to each of the six reagent domains thus obtained, a well-graduated colour change is produced after about 1 min, which can be calibrated and measured by reflectance photometry in conventional manner. The visual detection limit is ca. 10 ng of sarcosine/µl.

This Example shows that, according to the invention, even an analysis element working with relatively large amounts of reagent for an enzymatic test can easily be prepared. Compared with conventional tests, there is a significant saving on reagent and it is possible to work with a very small amount of sample. The low detection limit shows that the enzymatic activity has been virtually completely retained.

EXAMPLE 4

An analysis of the thyroid hormone TSH is performed on the one hand with a conventional immunoanalysis system (Enzymunsystem ES 22 from Boehringer Mannheim GmbH, Experiment A) and on the other hand with a system modified according to the invention (Experiment B). The individual steps for Experiment B are as follows:

a) Streptavidin-coated polystyrene tubes (manufactured according to EP-A-0344578) are used. 100 µl of sample or standard are metered into each tube.

b) 10 µl of a conjugate solution which has been filtered on a 0.8 µm filter are applied using a printing head as in Examples 1–3. The conjugate solution contains 18 U/ml of a conjugate consisting of a monoclonal antibody directed against TSH (ECACC 87122202) and peroxidase in 80 mM sodium phosphate buffer (NaPB) pH 7.4.

c) 1 min after delivery of the conjugate, 1 ml of incubation buffer (80 mM NaPB pH 7.4 with 1250 µg/ml of a biotinylated monoclonal antibody directed against TSH (ECACC 87122201), 2 g/l of bovine serum albumin and 1 g/l of bovine IgG) is metered via the metering unit of said system. (The biotinylation of the antibody was carried out in accordance with JACS 100 (1978, 3585–3590) by reaction with N-hydroxysuccinimidobiotin in a ratio of 10:1.)

d) The mixture is then incubated for 60 min.

e) Five washing steps, each consisting of aspiration of the reagent solution and metering of tap water, are carried out with the metering unit of the system used.

f) 1 ml of Enzymun-ABTS® substrate solution is metered, again via the metering unit.

g) The mixture is incubated for 30 min.

h) The extinction of the substrate solution is measured at 405 nm using the system's photometric measuring device.

In the conventional comparison (Experiment A), steps b and c are combined. In this case, the conjugate of step b is added in a concentration of 18 U/ml in the incubation buffer described under step c. 1 ml of this combined solution is metered via the metering unit of the system.

Calibration is carried out with conventional standards of between 0 and 51.1 µU of TSH/ml.

TABLE 3

| Precision/recovery of control sera | Experiment B | Experiment A |
|---|---|---|
| x (µU/ml) | 1.8 | 1.99 |
| CV (%) | 3.1 | 2.9 |
| x (µU/ml) | 5.74 | 6.26 |
| CV (%) | 4.8 | 3.2 |

Table 3 gives the results for two different nominal values (1.9 µU/ml and 6.0 µU/ml) with 12 measurements in each case, on the one hand for the modified procedure according to the invention and on the other hand for the comparative experiment. Comparable results are obtained in respect of precision and recovery of the nominal value.

Figure 4:
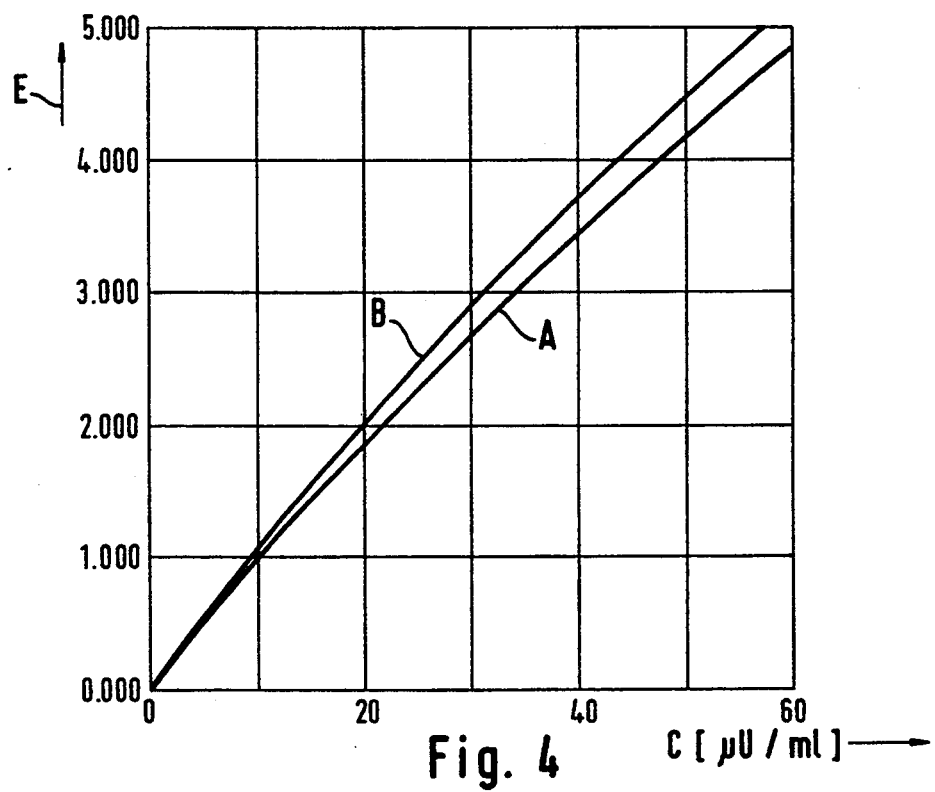
FIG. 4 shows two calibration curves pertaining to Example 4.

FIG. 4 shows the calibration curves for Experiments A and B, i.e. the extinction E as a function of the concentration of standard solutions. The fact that the two curves match very closely is further evidence that the properties of protein-containing solutions, namely of the antibody-enzyme conjugate in the present case, are virtually unchanged by application using the method according to the invention.

This result proves especially that the method according to the invention is suitable for the metering of very small quantities of liquid reagent, because the analyte TSH is present in an extremely low concentration.

What is claimed is:

1. A method for the metered application of a biochemical analytical liquid containing a heat-sensitive protein to a target, comprising the step of successively ejecting a plurality of quantities of the biochemical analytical liquid with high frequency from a jet chamber through a jet associated therewith onto the target by rapidly heating said biochemical analytical liquid by a heating element which is in thermal contact with said chamber for evaporating and expanding a part of the volume of the biochemical analytical liquid in the jet chamber so as to eject a predetermined quantity of the biochemical analytical liquid through the jet, wherein a majority of the heat-sensitive protein is not destroyed or denatured.

2. The method of claim 1, wherein the biochemical analytical liquid is a liquid reagent.

3. The method of claim 2, wherein the target is an analysis element reagent domain, a plurality of quantities of the biochemical analytical liquid reagent are successively ejected in droplet form to form dots in predetermined patterns on the reagent domain, and the jet and the analysis element are moved relative to one another in a manner such that the dots produced by the liquid reagent droplets on the reagent domain form a predetermined pattern in the reagent domain.

4. The method of claim 3, wherein a given dot produced by a droplet of liquid reagent on the reagent domain has a surface area of less than 2 mm$^2$.

5. The method of claim 3, wherein a plurality of different liquid reagents are each ejected from a separate jet chamber through separate jets onto the target.

6. The method of claim 5, wherein predetermined patterns produced from respective quantities of different liquid reagents applied to the reagent domain are essentially out of direct contact with adjacent predetermined patterns.

7. The method of claim 6, wherein the quantities of different liquid reagents form a pattern of alternating dots wherein quantities of different liquid reagents are adjacent to but spatially separated from each other.

8. The method of claim 1, wherein the protein contained in the biochemical analytical liquid is a member selected from the group consisting of an enzyme, an antibody, an antibody-enzyme conjugate, an antigen, and a hapten.

9. The method of claim 8, wherein the biochemical analytical liquid contains a binding protein.

10. The method of claim 1, wherein the target is a reaction vessel into which the biochemical analytical liquid is introduced.

11. The method of claim 1, wherein the biochemical analytical liquid which is ejected through the jet is in the form of a droplet and the biochemical analytical liquid which is evaporated and expanded is evaporated and expanded such that the increase in volume of the biochemical analytical liquid caused by the expansion is substantially the same as the volume of the droplet.

12. The method of claim 1, wherein the biochemical analytical liquid is member selected from the group consisting of a body fluid, a liquid reagent reactable with a body fluid, and a calibrating liquid.

13. The method of claim 12, wherein the target is a test carrier.

14. The method of claim 13, wherein the predetermined quantity of liquid ejected through the jet is no more than 2000 picoliters.

15. A method of analyzing a biological sample by measuring a physically measurable change caused by the reaction between a biological sample and a reagent containing a heat-sensitive protein which comprises the steps of:

ejecting a drop of the reagent through a jet of a jet chamber onto an analysis element by rapidly heating, evaporating and expanding a part of the volume of the reagent contained in the jet chamber, wherein said volume part is expanded in volume by an amount substantially corresponding to the volume of the drop and wherein a majority of the heat-sensitive protein in the reagent is not destroyed or denatured, bringing the sample into contact with the reagent on the analysis element to cause said reaction, and measuring said change.

16. A method of analyzing a biological sample by measuring a physically measurable change caused by the reaction between a biological sample and a liquid reagent containing a heat-sensitive protein comprising the steps of:

successively ejecting a plurality of quantities of said liquid reagent from a jet chamber through a jet associated therewith onto an analysis element reagent domain by heating, evaporating and expanding a part of the volume of the liquid reagent contained in the jet chamber, the plurality of quantities of the liquid reagent being successively ejected in droplet form to form dots on the reagent domain, the jet and the analysis element being moved relative to one another in a manner such that the dots produced by the liquid reagent droplets on the reagent domain form a predetermined pattern on the reagent domain and a majority of the heat-sensitive protein in the reagent not being destroyed or denatured;

conveying the analysis element to a sample delivery station;

bringing a sample into contact with the dots on the reagent domain; and measuring any physically measurable change which occurs as a result of a reaction between the sample and the reagent.

* * * * *